United States Patent [19]

Gorelick

[11] 4,116,230

[45] Sep. 26, 1978

[54] BLOOD PRESSURE CUFF AUTOMATIC DEFLATION DEVICE

[76] Inventor: Donald E. Gorelick, 43 Royal Crest Dr., Nashua, N.H. 03060

[21] Appl. No.: 722,135

[22] Filed: Sep. 10, 1976

[51] Int. Cl.² .............................................. A61B 5/02
[52] U.S. Cl. ............................................ 128/2.05 M
[58] Field of Search ................... 128/2.05 A, 2.05 C, 128/2.05 G, 2.05 M, 214 E, DIG. 13, 2.05 Q

[56] References Cited

U.S. PATENT DOCUMENTS

| | | | |
|---|---|---|---|
| 3,482,565 | 12/1969 | Gowen | 128/2.05 A |
| 3,552,383 | 1/1971 | Krueger | 128/2.05 A |
| 3,593,579 | 7/1969 | Hindman | 128/214 E |
| 3,609,379 | 5/1969 | Hildebrandt | 128/214 E |
| 3,623,052 | 11/1971 | Spiller | 128/DIG. 13 |
| 3,654,915 | 4/1972 | Sanctuary | 128/2.05 M |
| 3,655,095 | 4/1972 | Kienitz | 128/214 E |
| 3,736,930 | 6/1973 | Georgi | 128/DIG. 13 |
| 3,905,353 | 9/1975 | Lichowsky | 128/2.05 M |

Primary Examiner—Robert W. Michell
Assistant Examiner—Francis J. Jaworski
Attorney, Agent, or Firm—Schiller & Pandiscio

[57] ABSTRACT

A novel device for automatically deflating a blood pressure cuff with a standard two way valve is disclosed. An adjustable deflation rate consistent with normally accepted medical practice of two or three millimeters per heartbeat may be maintained. A two state valve and associated control circuitry for maintaining a constant deflation rate are described. This allows accurate sensing of Korotkoff sounds at different pressure levels.

10 Claims, 4 Drawing Figures

BLOOD PRESSURE CUFF AUTOMATIC DEFLATION DEVICE

BACKGROUND OF THE INVENTION

This invention generally relates to the medical arts and particularly concerns an automatic method for determining blood pressure. The medical arts have long recognized the need to measure arterial blood pressure as an indication of the general health of a patient.

The "auscultatory" method of blood pressure determination practiced by most physicians requires an inflatable blood pressure cuff, a pressure gauge and a stethoscope. The cuff is inflated until all blood flow in a limb has been stopped. Then the pressure is slowly released, by means of a manually operated needle valve, while the operator listens for Korotkoff sounds with a stethoscope placed on the skin over the occluded artery. The first Korotkoff sound usually appears at the systolic pressure, when the blood just begins to spurt through the occluded artery. The Korotkoff sounds continue, usually one occuring with each heartbeat until the pressure in the cuff is equivalent to the diastolic pressure. At this time, free blood flow is restored, and no further Korotkoff sounds are heard. This procedure is time consuming and requires a skilled attendant to accurately measure blood pressure. For this reason, the prior art has developed a multitude of instrumentation for automatic or semiautomatic determination of blood pressure. Such instrumentation may be applied internally and externally to the patient. An example of an internal blood pressure monitor includes those devices wherein penetration of the skin by means of a needle or the like through the arterial wall is effected. The pressure of the arterial pulse thereby being directly measured via a suitable pressure transducer. Such internal techniques risk the discomfort and infection of the patient and are certainly unsuitable for routine blood pressure checks. Externally applied instrumentation normally consists of a blood pressure cuff which is to apply pressure to the limb of the patient so that the arterial flow will be restricted. A suitable transducer similar to a stethoscope used in manual operation is then used to distinguish Korotkoff sounds which occur when the cuff pressure is between systolic and diastolic pressures. Many of these instruments require cuff inflation and deflation by a skilled operator by means of a bulb with a check valve for inflation and a needle valve for deflation. Recommended deflation rates for most accurate blood pressure measurement is between two and three millimeters of Mercury per heartbeat. To attain these rates an operator must continually adjust the needle valve because of the change in cuff volume. This requires the operators complete attention during the bleed procedure. Typically, some automatic blood pressure machines will have a light or audible signal emitted with each Korotkoff sound, so by remembering at what point of pressure the sounds appeared and disappeared the blood pressure may be noted. More sophisticated equipment automatically inflates the cuff and deflates the cuff at a fairly consistent rate by means of a pressure pump and a variable orifice bleed valve. The disadvantage of this method is the high cost of the variable orifice valve and control circuitry.

BRIEF DESCRIPTION OF THE DRAWINGS

FIG. 3 is the valve opening pulse width control, while FIG. 4 shows the circuitry used for the determination and control of the bleed rate.

DETAILED DESCRIPTION OF THE PREFERRED INVENTIVE EMBODIMENT

Figure 1:
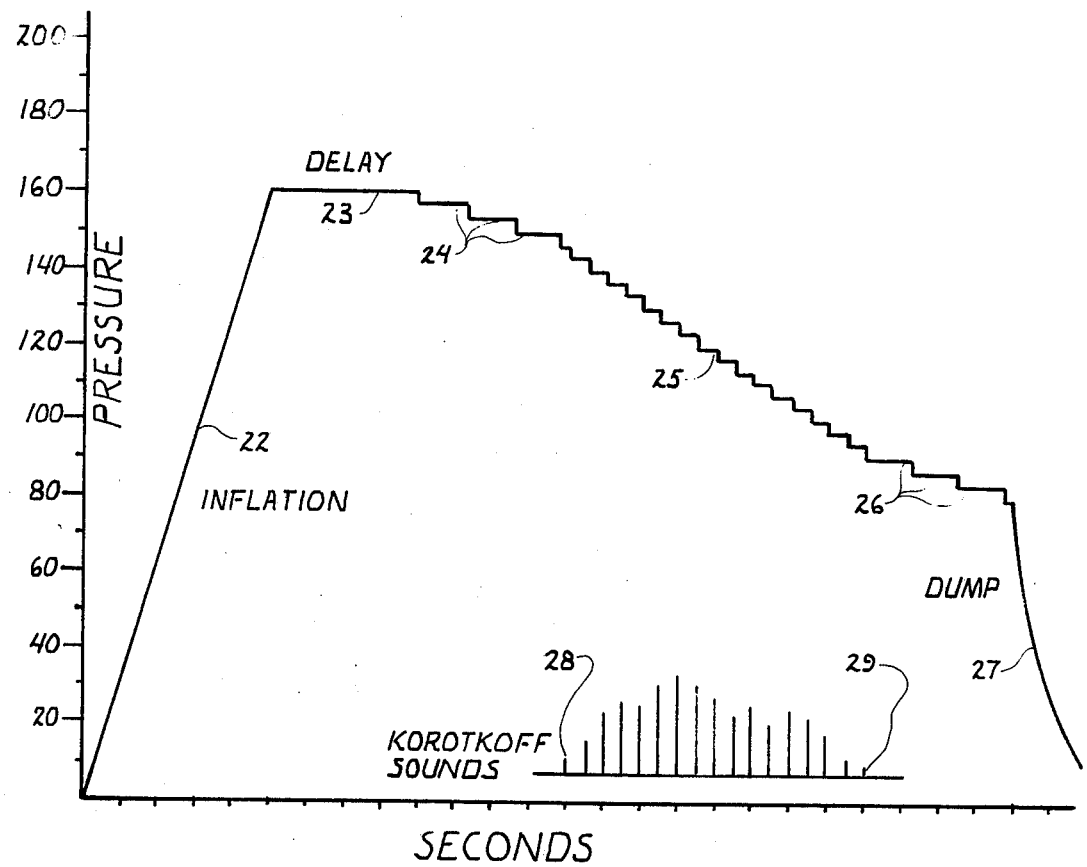
FIG. 1 shows in graphical form the time relationship of the cuff pressure and the Korotkoff sounds, during a typical inflation and deflation cycle.

To better understand the preferred inventive embodiment, it may be helpful to describe the relationship of Korotkoff sounds to cuff pressure and time during a pressure cycle. FIG. 1 shows a graph of arm cuff pressure verses time and an electrical analog signal representation from a transducer placed over the brachial artery. The cuff is inflated 22 by any of a variety of means, so that the cuff pressure is above the systolic pressure. As the cuff pressure is decreased, the first Korotkoff sound 28 appears at the systolic pressure, and the last Korotkoff sound 29 appears at the diastolic pressure.

The pressure deflation cycle is shown as it appears when it is controlled by the preferred inventive embodiment. After the inflation period, there is a delay 23 of a few seconds useful for determining if the pressure is above systolic (by the absence of Korotkoff sounds). The bleed begins after this, and the valve controlled by the control module is opened to allow a short pulse of air flow from the cuff thereby reducing the pressure in the cuff by a finite amount. The valve here is shown to have opened every 1.25 seconds 24 until the first systolic sound 28 appears and is detected by a Korotkoff sound processor. The period of 1.25 seconds or similar is chosen to reduce any possibilities that a valve opening may coincide with more than one Korotkoff sound, because each valve opening applies artifacts to the Korotkoff sound transducer which are often indistinguishable from Korotkoff sounds. After the first Korotkoff sound is detected, the valve openings are triggered by each successive Korotkoff sound.

SUMMARY OF THE INVENTION

As is apparent, a need exists in the art for an improved technique for automatically bleeding a pressure cuff at a rate consistent with medical recommendations of two or three millimeters of mercury per heartbeat. The primary objective of the instant invention is the control of bleed rate from a pressure cuff using an electronically controlled two way (either open or closed) valve, since these valves are comparatively low in price and readily available.

A further objective of the instant invention is the accurate control of the period and frequency the bleed valve is opened, so that a consistent bleed rate results.

A further objective of the instant invention is the complete venting of the cuff after it is determined that the probability of other Korotkoff sounds is small. This will be the diastolic blood pressure.

Still another object of the instant invention is timing the valve openings so that the periods in which the valve is opened will least interfere with the detection of Korotkoff sounds.

A further object of the instant invention is to disable any Korotkoff sound detection circuitry during the period that the valve is opened so that the pressure spurts will not be detected as Korotkoff sounds.

These objects, as well as others which will become apparent as the description proceeds are implemented by the instant inventive cuff deflation device which in its general form consists of a valve and pressure sensing device connected to a pressure tube leading to the blood pressure cuff. Control circuitry is provided to control the frequency and the period of time the valve is opened to allow a consistent and repeatable bleed rate. The bleed then becomes a series of accurate step decreases in pressure.

If the Korotkoff sounds cease or there is more than 1.25 seconds occurring between Korotkoff sounds, the circuitry automatically will open the valve every 1.25 seconds for a predetermined number of openings. This period 26 is useful in case one or more Korotkoff sounds between systolic and diastolic are missed by the processing circuitry. After the predetermined number of openings 26 occur, the valve is opened for a long "dump" period 27 to allow venting of the remaining cuff pressure. This typically takes 8 to 15 seconds. In each preceding valve opening pulse, the pulse width for consistent bleed rate is determined by the control circuitry to allow for changes in cuff capacitance due to limb diameter and cuff pressure.

Figure 2:
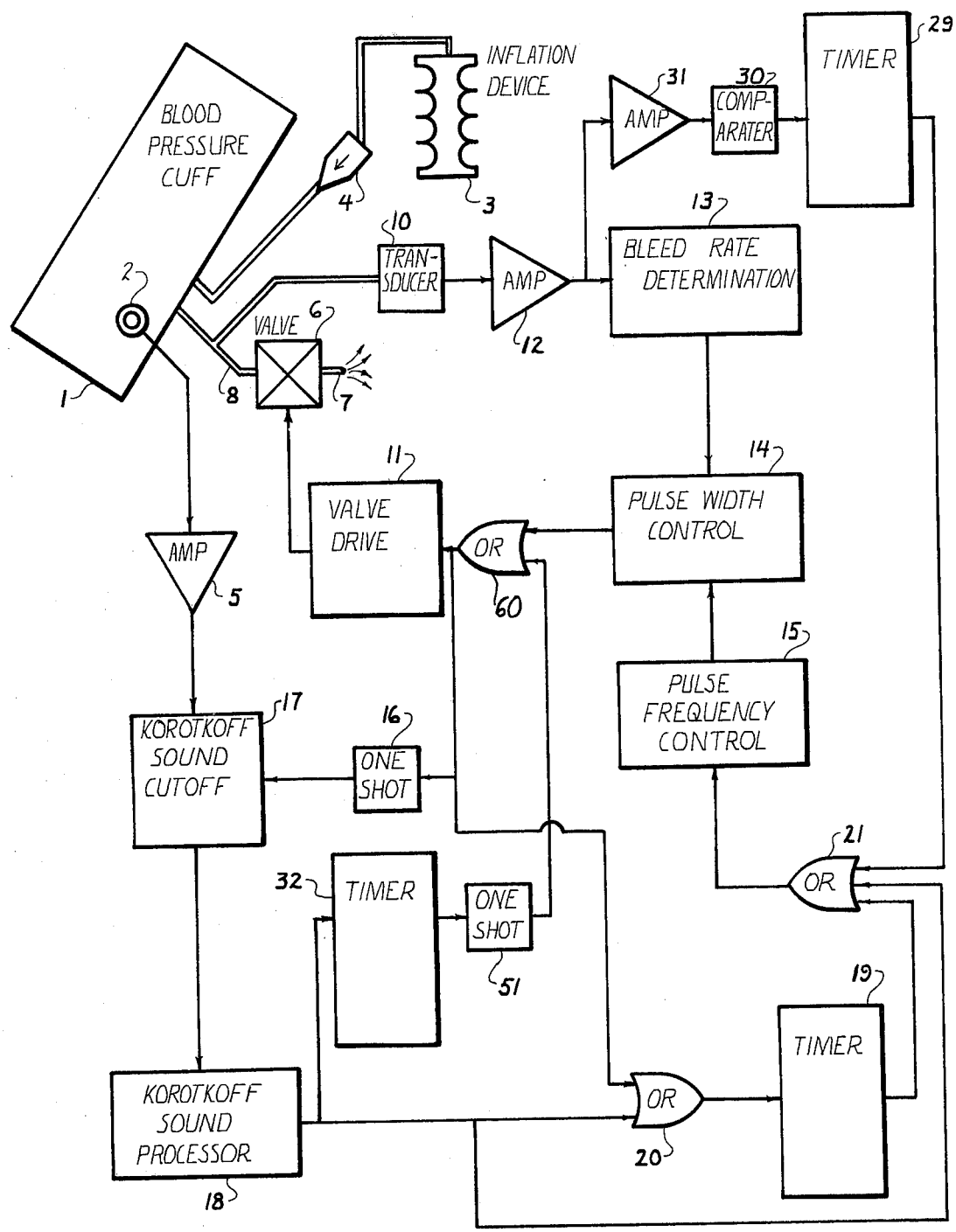
FIG. 2 is a diagrammatic view of a preferred embodiment of the bleed control system according to the present invention, illustrating the complete cuff deflation system.

Referring now to FIG. 2, a diagrammatic view of the preferred inventive embodiment of the cuff deflation device, the blood pressure cuff 1 may be inflated by a suitable inflation device 3, through check valve 4. During the inflation period the valve 6 is closed, to allow for complete inflation. After inflation has stopped there are no further AC signals from the pressure transducer 10 large enough after amplification 12 and 31 to trigger comparator 30. This allows the timer 29 to initiate, after a preset delay, a firing pulse to OR gate 21 which controls the frequency of valve opening signals. The pulse frequency control 15 triggers the firing of a valve opening pulse, whose width is controlled by controllers 14 and 13 to be described in more detail following. The valve drive pulse also serves an important function which is to trigger the one shot 16 which inhibits the detection of Korotkoff sounds through cut-off 17. The Korotkoff sound cut-off 17 can be any of a number of different devices, preferably a CMOS transmission gate. This assures that the sudden decrease in cuff pressure due to the valve opening which necessarily stimulates the Korotkoff sound transducer 2 and is amplified by 5, does not fool the Korotkoff sound processor 18. The short length of the valve opening period and the accurate control of valve timing as described previously assures that the Korotkoff sound cut-off 17 will not inhibit more than one Korotkoff sound if it happens to occur synchronously with the valve opening period.

Valve opening pulses once triggered by the timer 29 then continue every 1.25 seconds or other period as set in 19 until the Korotkoff sound processor 18 determines Korotkoff sounds have occurred and outputs a pulse coincident with each Korotkoff sound detected. These cause triggering of OR gate 21 controlling the valve opening pulse frequency and reset timers 19 and 32. When no further Korotkoff sounds are detected, or if one or more are missed by the detector, the timer 19 initiates valve opening pulses until the time out of timer 32 which initiates a valve opening for a period set by one shot 51 long enough to vent the remaining cuff pressure.

Valve opening pulses initiated by OR gate 21 and controlled in width by controller 14, control the valve driver 11, a standard transistor interface which causes valve 6 to open allowing a brief burst of air to exit cuff 1 through pressure line 8 to ambient port 7. OR gate 60 passes either one shot 51 pulses or controller 14 pulses to the valve driver 11. By controlling the length of time the valve is opened (the pulse width) by 14 an accurate cuff bleed consisting of a number of controlled pressure decreases is made possible. A typical inflation, deflation cycle is shown in FIG. 1. The control of the valve opening period may be made by a feedback type control 13 whereby the opening period can be controlled by an analog or digital signal proportional to the bleed rate. A specific preferred embodiment is better illustrated in FIGS. 3 and 4.

Figure 3:
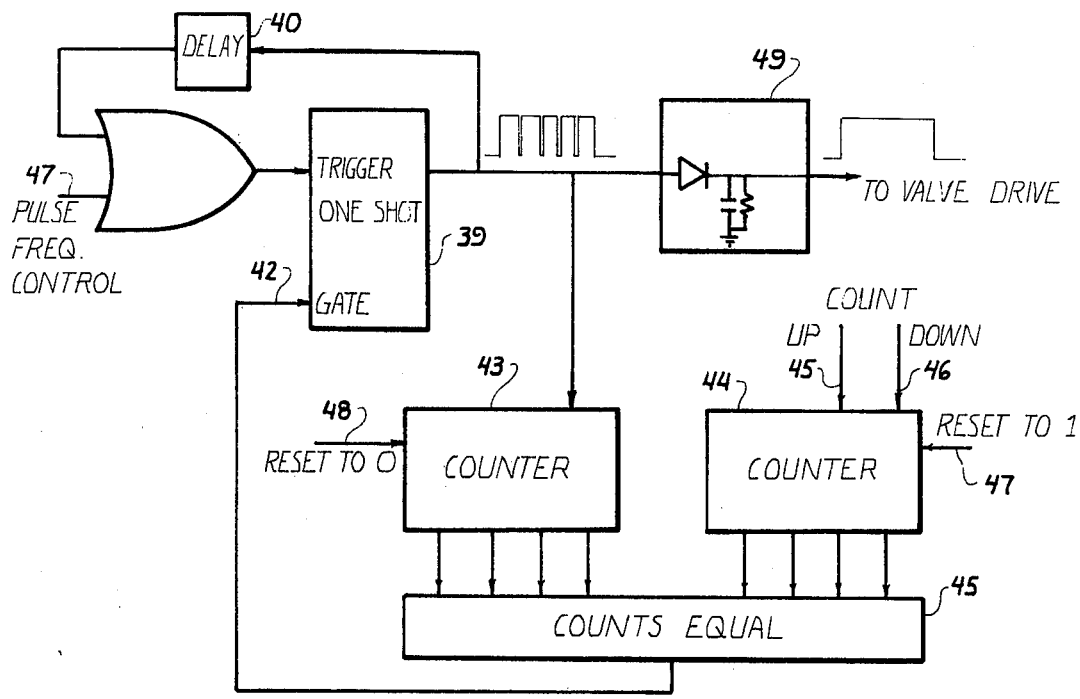
FIGS. 3 and 4 show two subsections of a preferred embodiment for the control of the valve opening period.

FIG. 3 shows a preferred embodiment of a method to control pulse width of the valve opening period. The method illustrated is a digital technique to give a total pulse width equal to the sum of a fixed number of smaller pulses produced in a retriggerable monostable (one shot multivibrator) 39. An analog pulse width modulator may, of course, be used here with equal success. The digital technique requires a trigger pulse from the Pulse Frequency Control line 47. This will trigger one shot 39 as long as gate control line 42 remains high in voltage. Each pulse from one shot 39 advances counter 43 which is preset to zero before each valve opening period by control line 48. The trailing edge of each one shot pulse is delayed by resistor and capacitor network 40 so that the monostable 39 will automatically retrigger itself as long as gate control line 42 is high. Gate control line 42 is driven by a decoding network of standard digital logic gates which determines if the count of counter 43 is equal to the count of counter 44. When the counts are equal the gate control line 42 is driven low so that no further one shot pulses may occur until counter 43 is reset to zero prior to the next valve opening period. To allow at least one monostable pulse for each valve opening, counter 44 is required to be always at least a count of one. This may be easily obtained by a suitable digital network 47 which presets the counter to one before each cuff bleed cycle. The number of monostable pulses which combine to form the valve opening period is therefore determined by the count in counter 44. The control lines 45 or 46 may be enabled after each valve opening period if the control system determines the pressure change caused by the last valve opening was too great or too small. The train of pulses from monostable 39 are filtered by diode, resistor, capacitor network 49 so that the output pulse is a single pulse equal in length to the sum of all the monostable pulses. This controlled length pulse then drives the valve driver.

Figure 4:
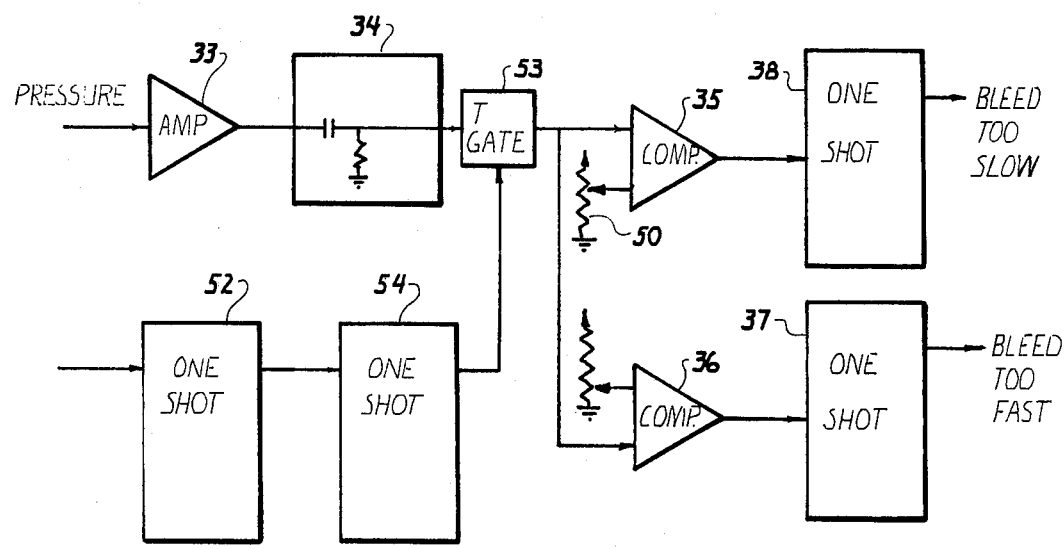

The control of counter 44 requires a system similar to the one shown in FIG. 4 of the Bleed Rate Determination network. This may take the form of an inverting amplifier 33 followed by a differentiator 34, transmission gate 53, and comparaters 35 and 36. The decrease in pressure sensed by the pressure sensor after each valve opening is converted to a positive going pulse, whose amplitude varies with the pressure change. Comparator 35 and 36 are triggered by a pulse from differentiator 34 which is higher or lower than a preset standard, and which also occurs after a period determined by delay 52 after the valve opening period. Delay 54 enables the input to the comparators only a short instant after delay 52 after the end of the valve opening period. The comparators each drive edge triggered one shots 37 and 38 which cause counter 44 to either count up or down depending respectively on whether the valve opening period was too short or too long. In many applications, comparator 36 and one shot 37 may not be needed since the valve opening periods will normally just require increasing as cuff pressure decreases. By adjusting control 50, the pressure steps may be accurately preset to enable more rapid cuff deflation if measurement speed rather than accuracy is of prime consideration.

Accordingly what is claimed is:

1. Apparatus for measuring blood pressure of a patient, comprising in combination:
   (A) an inflatable cuff for mounting on a patient;
   (B) inflation means connected to said cuff for inflating said inflatable cuff with air to above systolic pressure;
   (C) an electrically controlled two state valve connected to said cuff for bleeding air from said inflatable cuff in a controlled manner;
   (D) pressure transducer connected to said inflatable cuff for generating a signal as a function of the air pressure in said cuff;
   (E) sound sensing means for detecting Korotkoff sounds while air is being bled from said inflatable cuff; and
   (F) control means connected between said pressure transducer and said electrically controlled valve for controlling the (1) frequency and (2) period of valve openings so as to produce a relatively consistent bleed rate, said control means including (a) timing means for triggering valve openings for predetermined finite periods until said systolic pressure is reached; (b) means responsive to said Korotkoff sounds for triggering valve openings as a function of said Korotkoff sounds; (c) bleed rate determination means for comparing pressure drop caused by each said valve opening to a known reference value; (d) means for correcting the duration and frequency of said valve openings in response to signals from said pressure transducer; and
   (e) means responsive to said means for correcting generating signal pulses for opening said valve.

2. Apparatus of claim 1 wherein the width of said opening pulses is determined by the sum of pulses from a retriggerable one shot monostable multivibrator.

3. Apparatus of claim 2, wherein said one shot pulses are counted and compared digitally to a similar counter whose count is controlled by a pulse width correction circuit.

4. Apparatus of claim 3 wherein said pulse width correction circuit comprises a one shot multivibrator which is triggered when too slow a bleed rate is detected by said bleed rate determination circuit.

5. Apparatus of claim 1 wherein the frequency of said valve opening pulses is so adjusted to occur (a) either immediately following each detected Korotkoff sound or (b) at a predetermined spacing when no Korotkoff sounds are present.

6. Apparatus of claim 1, wherein said bleed rate determination means comprises:
   (a) a differentiation circuit adapted to provide a signal proportional to the pressure change with each said valve opening; and
   (b) a comparator circuit adapted to provide an output signal when said differentiated signal is different than said reference value.

7. Apparatus of claim 6, and further comprising a comparator circuit adapted to provide an output signal when said differentiated signal is greater than said reference value.

8. Apparatus of claim 6, and further comprising a comparator circuit adapted to provide an output signal when said differentiated signal is less than said reference value.

9. Apparatus of claim 1, wherein said valve means is adapted to rapidly vent any remaining cuff pressure when no further Korotkoff sounds are detected.

10. Apparatus of claim 9 further including means for delaying said bleed following cuff inflation.

* * * * *